(12) United States Patent
Lulla et al.

(10) Patent No.: US 7,517,519 B2
(45) Date of Patent: Apr. 14, 2009

(54) TOPICAL IMMUNOTHERAPY AND COMPOSITIONS FOR USE THEREIN

(75) Inventors: Amar Lulla, Maharashtra (IN); Geena Malhotra, Maharashtra (IN)

(73) Assignee: Cipla Limited, Mumbai (IN)

( * ) Notice: Subject to any disclaimer, the term of this patent is extended or adjusted under 35 U.S.C. 154(b) by 224 days.

(21) Appl. No.: 10/544,724

(22) PCT Filed: Feb. 6, 2004

(86) PCT No.: PCT/GB2004/000474

§ 371 (c)(1),
(2), (4) Date: Oct. 31, 2005

(87) PCT Pub. No.: WO2004/069247

PCT Pub. Date: Aug. 19, 2004

(65) Prior Publication Data

US 2006/0204446 A1    Sep. 14, 2006

(30) Foreign Application Priority Data

Feb. 6, 2003  (IN)  .................. 170/MUM/2003

(51) Int. Cl.
*A61K 8/00*  (2006.01)

(52) U.S. Cl. .................. 424/70.1; 424/47; 424/184.1; 514/536

(58) Field of Classification Search .................. None
See application file for complete search history.

(56) References Cited

U.S. PATENT DOCUMENTS

| | | | | |
|---|---|---|---|---|
| 5,635,161 | A * | 6/1997 | Adjei et al. | .................... 424/45 |
| 6,184,248 | B1 | 2/2001 | Lee et al. | |
| 6,187,756 | B1 | 2/2001 | Lee et al. | |
| 6,579,901 | B2 * | 6/2003 | Chen et al. | ................... 514/455 |
| 2002/0013340 | A1 * | 1/2002 | Peyman | ...................... 514/310 |
| 2002/0052407 | A1 | 5/2002 | Lee et al. | |
| 2002/0173516 | A1 | 11/2002 | Chen et al. | |

FOREIGN PATENT DOCUMENTS

| | | |
|---|---|---|
| EP | 0544391 | 6/1993 |
| EP | 1092429 | 4/2001 |
| GB | 2 316 074 A * | 2/1998 |
| GB | 2316074 | 2/1998 |
| WO | 9809523 | 3/1998 |
| WO | 9951215 | 10/1999 |

OTHER PUBLICATIONS

Carelli, 2002, JAOCS, 79(8), 763-768.*

* cited by examiner

*Primary Examiner*—Andrew D Kosar
*Assistant Examiner*—Satyanarayana R Gudibande
(74) *Attorney, Agent, or Firm*—Novak Druce & Quigg, LLP

(57) ABSTRACT

The present invention is concerned with the use of at least one immunosuppressant, or a pharmaceutically acceptable salt, solvate of physiologically functional derivative thereof, in the treatment of topical immune disorders of the scalp, and scalp conditions, and compositions suitable for such use.

21 Claims, No Drawings

TOPICAL IMMUNOTHERAPY AND COMPOSITIONS FOR USE THEREIN

This application is a §371 National Stage Application of International Application No. PCT/GB2004/000474, filed on 6 Feb. 2004, claiming the priority of Indian Patent Application No. 170/MUM/2003 filed on 6 Feb. 2003.

The present invention is concerned with topical immunotherapy and compositions suitable for use therein.

Topical immunotherapy can be used to describe topical treatment with an agent having immunomodulatory properties. Recently, topical formulations including agents with direct immunosuppressive actions have been tested in diseases believed to have an immunological basis, especially atopic dermatitis and psoriasis. These topical immunosuppressive agents have included tacrolimus and structurally related asomycin derivatives.

Tacrolimus is a hydrophobic macrolide immunosuppressant produced by *Streptomyces tsukubaensis* No. 9993. Tacrolimus, 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4.9}$] octacos-18-ene-2,3,10,16-tetraone, which is also known as FK-506 or FR-900506, has the following structural formula:

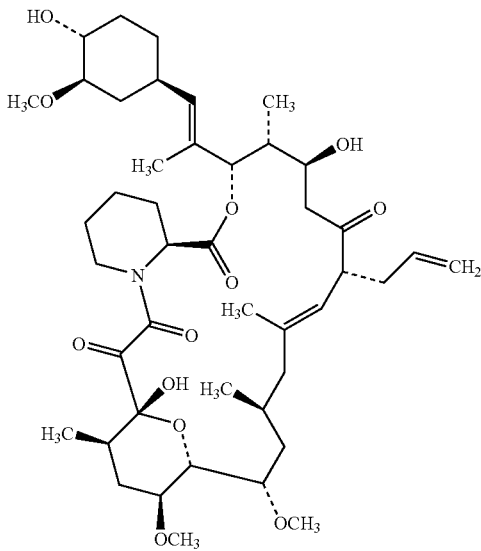

Tacrolimus inhibits T-lymphocyte activation by first binding to an intracellular protein, FKBP-12. A complex of tacrolimus-FKBP-12, calcium, cadmodulin and calcineurin is then formed and the phosphatase activity of calcineurin is inhibited. The effect has been shown to prevent the dephosphorylation and translocation of nuclear factor of activated T-cells (NF-AT), a nuclear component thought to initiate gene transcription for the formation of lymphokines (such as interleukin-2, gamma interferon). Tacrolimus also inhibits the transcription for genes which encode IL-3, IL-4, IL-5, GM-CSF and TNF-alpha, all of which are involved in the early stages of T-cell activation. Tacrolimus inhibits proliferation and selective cytokine expression in antigen stimulated T cells in culture and also inhibits B cell proliferation at similar concentrations. Immunosuppression with tacrolimus in humans prevents allograft rejection.

More particularly, tacrolimus inhibits T-lymphocyte activation, having a direct effect on T-lymphocytes so as to inhibit IL-2 transcription, which decreases responsiveness of T-lymphocytes to foreign antigens. The action of tacrolimus on atopic dermatitis may be related to alteration of antigen presenting cells, suppression of IL-2 and co-stimulatory molecule expression, impairment of phenotypic and functional differentiation of epidermal Langerhans' cells and suppression of Th1 and Th2 cytokine induction in lymph node cells. The effect of tacrolimus on pruritis may be related to inhibition of histamine release from skin mast cells and impairment of de novo mast cell prostaglandin D2 synthesis along with diminished release of histamine from basophiles.

Immunosuppression with tacrolimus in humans prevents allograft rejection. Tacrolimus is also reported as being used in the treatment of rejection in transplantation and autoimmune diseases, and is routinely used in transplantation of for example, the kidney, liver or heart.

Tacrolimus is available in both intravenous and oral formulation for the prevention of organ rejection after allogeneic liver or kidney transplantation. Oral tacrolimus has been found to be useful in the treatment of psoriasis, but potentially serious side effects, such as nephrotoxicity and hypertension, has limited its use for dermatologic indications by this route of administration. Topical formulations (ointments) have been extensively studied and reported to show positive effects in treatment of inflammatory skin diseases, such as atopic dermatitis and psoriasis. Tacrolimus administered topically (as an ointment) has been reported to be safe and effective in the treatment of skin diseases. It has been further reported that in patients with atopic dermatitis, tacrolimus does not alter collagen synthesis and is not atrophogenic.

U.S. Patent Application 2002052407, U.S. Pat. Nos. 6,187,756, 6,184,248 and WO 98/09523 describe compositions of tacrolimus for use in neurological disorders and neurogenerative diseases.

EP 1092429 discusses pharmaceutical compositions and methods for treating immune response associated disorders.

U.S. Patent Applications 2002173516 and 2002013340 describe pharmaceutical compositions and methods for treating immune response associated diseases of the surface and anterior segment of the eye.

EP 1067926 and WO 99/51215 describe the use of tacrolimus as showing inhibitory activity on the production of nitric oxide.

Surprisingly, it has now been found that immunosuppressants as described herein are particularly useful for treating topical immune disorders of the scalp, and scalp conditions. The present invention is, therefore, directed to such treatment and to compositions suitable for such use.

According to the present invention, therefore, there is provided at least one immunosuppressant, or a pharmaceutically acceptable salt, solvate or physiologically functional derivative thereof, for use in the manufacture of a medicament for the treatment of topical immune disorders of the scalp, and scalp conditions.

An immunosuppressant suitable for use according to the present invention is preferably selected from the group consisting of tacrolimus, cyclosporin, or a pharmaceutically acceptable salt, solvate or physiologically functional derivative thereof.

The present invention also provides a method for the treatment or prophylaxis of topical immune disorders of the scalp, and scalp conditions, which method comprises topically administering to the hair and scalp of a patient suffering from, or susceptible to, topical immune disorders of the scalp, and scalp conditions, a therapeutically effective amount of at least one immunosuppressant, or a pharmaceutically acceptable salt, solvate or physiologically functional derivative thereof.

According to the above described method of the present invention, an immunosuppressant, or a pharmaceutically acceptable salt, solvate or physiologically functional derivative thereof, can be topically administered to the area of scalp affected by an immune disorder and as such exert a therapeutic effect thereto. The treatment regime will be dependent on the patient, and severity of the scalp condition being treated, and will generally be at the discretion of an attendant physician.

An immunosuppressant suitable for use in a method according to the present invention is preferably selected from the group consisting of tacrolimus, cyclosporin, or a pharmaceutically acceptable salt, solvate or physiologically functional derivative thereof.

The term "physiologically functional derivative" as used herein denotes a chemical derivative of an immunosuppressant as described herein having the same or similar physiological function as the free base immunosuppressant and, for example, being convertible in the body thereto.

Preferably, according to a use or method of the present invention, the immunosuppressant is administered to a patient in the form of a hair care composition, such as a cream, spray, gel, shampoo or mousse, with the use of a mousse composition generally being preferred.

Hair care preparations, and ingredients suitable for use therein, are of course well known. Such preparations are generally aimed at providing condition, shine, body and increased manageability to hair. There are recognized categories of hair care compositions, including creams, sprays, gels, shampoos or mousses as referred to above. Hair sprays are generally composed of aerosolized copolymers, such as polyvinylpyrrolidone, vinyl acetate and the like, and are generally applied following hair styling but may also function as a setting lotion. Hair gel preparations are similar to sprays in composition, but are in gel and alcohol free form, and can coat the hair shaft and restore shine.

Hair mousse is foam released under pressure from an aerosolized can. Mousses can contain glossening and conditioning agents and can be colored to provide highlights. Hair mousses can also be employed to provide fullness to hair, and achieve this more easily than hair gels due to their lower moisture content.

There is also provided by the present invention, therefore, a pharmaceutical composition formulated for topical application to the hair and scalp of a patient, which composition comprises at least one immunosuppressant, or a pharmaceutically acceptable salt, solvate or physiologically functional derivative thereof, together with at least one carrier therefor, wherein said immunosuppressant is included in said composition in a therapeutically effective amount so as to be capable of exerting a therapeutic effect on topical immune disorders of the scalp, and scalp conditions, when administered to a patient suffering therefrom.

A composition according to the present invention can be provided as a cream, spray, gel, shampoo or a mousse forming hair and scalp treatment composition. Preferably, however, a composition according to the present invention is provided in the form of a mousse forming hair and scalp treatment composition for immune disorders of the scalp, and scalp conditions, wherein the composition comprises at least one immunosuppressant, or a pharmaceutically acceptable salt, solvate or physiologically functional derivative thereof, together with at least one carrier therefor, and which is formulated so as to be foamable on dispensing from a housing in which the composition can be packaged for administration to a patient.

More particularly, there is provided by the present invention a pharmaceutical composition formulated for topical application to the hair and scalp of a patient, which comprises at least one immunosuppressant, or a pharmaceutically acceptable salt, solvate or physiologically functional derivative thereof, together with at least one carrier therefor, wherein said immunosuppressant is included in said composition in a therapeutically effective amount so as to be capable of exerting a therapeutic effect on topical immune disorders of the scalp, and scalp conditions, when administered to a patient suffering therefrom, and further characterised in that the composition is provided as a mousse forming hair and scalp treatment composition formulated so as to be foamable on dispensing from a housing in which the composition is packaged for administration to a patient.

Preferably, a mousse forming hair and scalp treatment composition according to the present invention further comprises at least one propellant. The propellant is the ingredient present in a mousse forming hair and scalp treatment composition according to the present invention which is responsible for expelling, on administration to a patient, the other ingredients of the composition from a housing containing the same. Typically the propellant can be selected from the group consisting of 1,1,1,2-tetrafluoroethane (HFA 134a), 1,1,1,2, 3,3,3-heptafluoroethane (HFA 227), a combination of 1,1,1, 2-tetrafluoroethane and 1,1,1,2,3,3,3-heptafluoroethane, monofluorotrichloromethane and dichlorodifluoromethane, and derivatives thereof, in particular 1,1,1,2-tetrafluoroethane (HFA 134a) or 1,1,1,2,3,3,3-heptafluoroethane (HFA 227). The use of 1,1,1,2-tetrafluoroethane (HFA 134a) is preferred.

Typically, a mousse forming hair and scalp treatment composition according to the present invention can further comprise one or more co-solvents. The composition may comprise both a propellant and a co-solvent, in which case it is desirable that the co-solvent has a greater polarity than the propellant. The co-solvent used may be any suitable solvent, and typical co-solvents for use in the present invention include $C_{2-6}$ aliphatic alcohols and polyols, for example ethanol, isopropanol and propylene glycol. Preferably the co-solvent is ethanol. Generally the co-solvent is present in the range of 5 to 50% by weight of the total composition.

Suitably, a mousse forming hair and scalp treatment composition according to the present invention may further comprise a surface-active agent to stabilize the composition and for the lubrication of a valve system employed in a hair and scalp treatment product according to the present invention substantially as hereinafter described. Some of the most commonly used surface-active agents in mousse compositions are oils derived from natural sources, such as corn oil, olive oil, cotton seed oil, sunflower seed oil, castor oil, cocoa butter, coconut oil, evening primrose oil, jojoba oil, linseed oil, palm oil, palm kernel oil, peanut oil and the like.

The immunosuppressant active ingredient in a mousse forming hair and scalp treatment composition according to the present invention is preferably present at a concentration of 0.1 wt % to 5 wt % of the total composition.

A mousse forming hair and scalp treatment composition according to the present invention may include further ingredients suitable for use in a hair care treatment composition of the type known in the art, and such further ingredients can include petrolatum, waxes, lanolin, vegetable and mineral oils, plasticizers, preservatives, or other suitable ingredient for a mousse composition. Such ingredients can add shine to hair and moisturize it, aid in straightening and decrease breakage, in addition to the topical immunotherapy achieved further to the presence of at least one immunosuppressant, or a pharmaceutically acceptable salt, solvate or physiologically functional derivative thereof, in the composition substantially as hereinbefore described. The formulation may further comprise colorants, fragrances and anti-oxidants, and silicone and functional derivatives thereof to add lubricity, castor oil and derivatives thereof to aid in manageability and soluble glycoprotein to maintain proper moisture balance and enhance shine.

A mousse forming hair and scalp treatment composition according to the present invention may be formulated as a hydrophobic or hydrophilic cream or gel, suitably with addition of a propellant known in the art and as described above.

The petrolatum and waxes are those commonly used by a person skilled in the art in cream formulations and may include petroleum bases and waxes obtained from natural and synthetic origin, such as beeswax, carnauba wax, cetomacrogol waxes, paraffin waxes, lanolin, wool fat, ozocerite and the like.

Mineral oils commonly used in mousse compositions include fatty acids, fatty alcohols, metallic stearates, monoalcohol esters, glycol esters, polyethylene glycol and its esters, sorbitan esters and the like.

Advantageously, a composition according to the present invention may be formulated substantially free of water, which can in certain embodiments of the present invention be beneficial in terms of the stability of an immunosuppressant (especially tacrolimus), or a pharmaceutically acceptable salt, solvate or physiologically functional derivative thereof, employed according to the present invention.

According to another aspect of the invention there is provided a hair and scalp treatment product, which comprises a composition substantially as hereinbefore described packaged in a housing (typically a can), provided with a dispensing mechanism for dispensing said composition to the hair and scalp of a patient. Preferably the dispensing mechanism, and the ingredients of a composition according to the present invention, are such that a mousse can be generated on dispensing from the housing.

The present invention also provides a process of preparing a composition as described herein, which process comprises providing at least one immunosuppressant, or a pharmaceutically acceptable salt, solvate or physiologically functional derivative thereof, in the form of a composition suitable for topical administration to the hair and scalp of a patient substantially as hereinbefore described.

The present invention will now be further illustrated by the following Examples, which do not limit the scope of the invention in any way.

EXAMPLES

Example 1

| Sr. No. | Ingredients | Quantity (% w/w) |
| --- | --- | --- |
| I | CREAM | |
| 1. | Tacrolimus | 0.1-5% |
| 2. | Polyethylene glycol 400 | 4.00 |
| 3. | Polysorbate 80 | 0.80 |
| 4. | Methyl paraben | 0.20 |
| 5. | Propyl paraben | 0.02 |
| 6. | Disodium edetate | 0.10 |
| 7. | Cetostearyl alcohol | 1.50 |
| 8. | Cetomacrogol 1000 | 0.50 |
| 9. | Light liquid paraffin | 5.00 |
| 10. | Dimethicone | 1.50 |
| 11. | Propylene glycol | 10.00 |

-continued

| Sr. No. | Ingredients | Quantity (% w/w) |
| --- | --- | --- |
| 12. | Triethanolamine | q.s. to pH 6.0 |
| 13. | Purified Water | q.s. to 90.0 |
| 14. | Ethanol | 5-50% |
| 15. | Polyoxyl hydrogenated castor oil | 2-20% |
| II | PROPELLANT | |
| 16. | Tetrafluoroethane (HFC-134a) | 10.00 |

Example 2

| Sr. No. | Ingredients | Quantity (% w/w) |
| --- | --- | --- |
| I | CREAM | |
| 1. | Cyclosporin | 0.1-5% |
| 2. | Polyethylene glycol 400 | 4.00 |
| 3. | Polysorbate 80 | 0.80 |
| 4. | Methyl paraben | 0.20 |
| 5. | Propyl paraben | 0.02 |
| 6. | Disodium edetate | 0.10 |
| 7. | Cetostearyl alcohol | 1.50 |
| 8. | Cetomacrogol 1000 | 0.50 |
| 9. | Light liquid paraffin | 5.00 |
| 10. | Dimethicone | 1.50 |
| 11. | Propylene glycol | 10.00 |
| 12. | Triethanolamine | q.s. to pH 6.0 |
| 13. | Purified Water | q.s. to 90.0 |
| 14. | Ethanol | 5-50% |
| 15. | Polyoxyl hydrogenated castor oil | 2-20% |
| II | PROPELLANT | |
| 16. | Tetrafluoroethane (HFC-134a) | 10.00 |

The ingredients as given above for Examples 1 and 2 were formulated so as to provide compositions according to the present invention, employing techniques known in the art.

The invention claimed is:

1. A pharmaceutical composition formulated for topical application to the hair and scalp of a patient, which composition comprises a therapeutically effective amount of at least one immunosuppressant selected from the group consisting of tacrolimus, cyclosporin, or a pharmaceutically acceptable salt thereof, together with at least one carrier therefor, wherein the composition is provided as a mousse forming hair and scalp treatment composition formulated so as to be foamable on dispensing, from a housing in which the composition is packaged for administration to a patient.

2. A composition according to claim 1, which further comprises at least one propellant.

3. A composition according to claim 2, wherein said propellant is selected from the group consisting of 1,1,1,2-tetrafluoroethane, 1,1,1,2,3,3,3-heptafluoroethane, a combination of 1,1,1,2-tetrafluoroethane and 1,1,1,2,3,3,3-heptafluoroethane, monofluorotrichloromethane and dichlorodifluoromethane, and derivatives thereof.

4. A composition according to claim 3, wherein said propellant is 1,1,1,2-tetrafluoroethane or 1,1,1,2,3,3,3-heptafluoroethane.

5. A composition according to claim 4, wherein said propellant is 1,1,1,2-tetrafluoroethane.

6. A composition according to claim 1, which further comprises one or more co-solvents.

7. A composition according to claim 1, wherein said co-solvent is present in the range of 5 to 50% by weight of the total composition.

8. A composition according to claim 1, which further comprises a surface-active agent.

9. A composition according to claim 8, wherein said surface-active agent is derived from natural sources including corn oil, olive oil, cotton seed oil, sunflower seed oil, castor oil, cocoa butter, coconut oil, evening primrose oil, jojoba oil, linseed oil, palm oil, palm kernel oil and peanut oil.

10. A composition according to claim 1, wherein said immunosuppressant is present at a concentration of 0.1 wt % to 5 wt % of the total composition.

11. A composition according to claim 1, which further comprises one or more of the following: petrolatum, waxes, lanolin, vegetable and mineral oils, plasticizers or preservatives.

12. A composition according to claim 11, wherein said petrolatum and waxes are selected from the group consisting of beeswax, carnauba wax, cetomacrogol waxes, paraffin waxes, lanolin, wool fat and ozocerite.

13. A composition according to claim 11, wherein said mineral oils are selected from the group consisting of fatty acids, fatty alcohols, metallic stearates, monoalcohol esters, glycol esters, polyethylene glycol and its esters and sorbitan esters.

14. A composition according to claim 1, which further comprises one or more colorants, fragrances, anti-oxidants, glossening and conditioning agents.

15. A hair and scalp treatment product, which comprises a composition according to claim 1 packaged in a housing provided with a dispensing mechanism for dispensing said composition to the hair and scalp of a patient.

16. A product according to claim 15, wherein said dispensing mechanism, and ingredients of said composition, are such that a mousse is generated on dispensing from the housing.

17. A process of preparing a composition according to claim 1, which process comprises providing at least one immunosuppressant, selected from the group consisting of tacrolimus, cyclosporin, or a pharmaceutically acceptable salt thereof, in the form of a mousse suitable for topical administration to the hair and scalp of a patient.

18. A method for the treatment of topical immune disorders of the scalp, and scalp conditions, which method comprises topically administering to the hair and scalp of a patient suffering from, topical immune disorders of the scalp, and scalp conditions, a composition according to claim 1.

19. A method according to claim 18, wherein said composition is topically administered to an area of scalp affected by said topical immune disorder so as to exert a therapeutic effect thereto.

20. A comoosition according to claim 1, wherein the composition is substantially free from water.

21. The hair and scalp treatment product according to claim 15, wherein the composition free from water.

* * * * *